(12) United States Patent
Williams, III et al.

(10) Patent No.: US 8,323,209 B2
(45) Date of Patent: Dec. 4, 2012

(54) CHORIONIC VILLUS SAMPLING CATHETER

(76) Inventors: John Williams, III, Los Angeles, CA (US); Jennifer Marie Williams, Los Angeles, CA (US)

( * ) Notice: Subject to any disclaimer, the term of this patent is extended or adjusted under 35 U.S.C. 154(b) by 221 days.

(21) Appl. No.: 12/455,517

(22) Filed: Jun. 3, 2009

(65) Prior Publication Data

US 2009/0306540 A1    Dec. 10, 2009

Related U.S. Application Data

(60) Provisional application No. 61/131,201, filed on Jun. 6, 2008.

(51) Int. Cl.
*A61B 10/00* (2006.01)
(52) U.S. Cl. .................. 600/562; 600/569; 600/570
(58) Field of Classification Search ............... 604/528, 604/95.04, 164.11; 600/585, 570, 562
See application file for complete search history.

(56) References Cited

U.S. PATENT DOCUMENTS

| | | | |
|---|---|---|---|
| 4,068,659 A * | 1/1978 | Moorehead | 604/508 |
| 4,737,153 A * | 4/1988 | Shimamura et al. | 604/526 |
| 4,756,708 A | 7/1988 | Martin | |
| 4,863,430 A * | 9/1989 | Klyce et al. | 604/170.03 |
| 5,090,419 A * | 2/1992 | Palestrant | 600/567 |
| 5,106,377 A | 4/1992 | Martin | |
| 6,042,562 A | 3/2000 | Amor | |
| D550,356 S | 9/2007 | Anderson et al. | |
| 7,465,288 B2 | 12/2008 | Dudley et al. | |
| 7,503,914 B2 | 3/2009 | Coleman et al. | |
| 2004/0181140 A1 | 9/2004 | Falwell et al. | |
| 2006/0106297 A1 | 5/2006 | Drysen | |
| 2008/0009882 A1 | 1/2008 | Drysen | |
| 2008/0275388 A1 | 11/2008 | Partlett et al. | |
| 2009/0024084 A1 | 1/2009 | Khosla et al. | |

FOREIGN PATENT DOCUMENTS

WO   WO 2008/014557 A1   2/2008

* cited by examiner

*Primary Examiner* — Jeffrey G Hoekstra
*Assistant Examiner* — Megan Leedy
(74) *Attorney, Agent, or Firm* — A. F. Davis Law; Albert F. Davis

(57) ABSTRACT

A catheter with a guide wire and handle is provided for sampling an area of interest, such as chorionic villi. The catheter contains a cannula of flexible plastic that is non-pyrogenic and latex-free, and a flexible obturator with an elongate cylindrical handle. The cannula is echogenic and can be easily visualized with visualization or imaging device. In an embodiment, the catheter may be curved manually by the operator to conform to the patient's anatomy and it is inserted through the cervix into a pregnant uterus at 10-13 weeks gestation and placed into the developing placenta under ultrasound guidance and a guide mechanism provided on the handle. In this embodiment, once the catheter has been placed, the obturator is withdrawn and a sample of chorionic villi is removed by applying appropriate pressure to the proximal end of the cannula and slowly withdrawing the cannula from the uterine cavity.

14 Claims, 2 Drawing Sheets

CHORIONIC VILLUS SAMPLING CATHETER

Related U.S. Application: Provisional application No. 61/131,201, filed on Jun. 6, 2008.

FIELD OF INVENTION

The present invention is directed to catheters for use in the chorionic villus sampling medical procedure.

BACKGROUND OF THE INVENTION

Chorionic villus sampling (CVS) is an established method for prenatal diagnosis of genetic diseases and birth defects in the first trimester of pregnancy, which has been in use since the 1980s. The procedure entails retrieving a sample of the chorionic villus or placental tissue and testing it. CVS is an alternative to genetic amniocentesis, a procedure used since the 1960s for essentially the same purpose, and may be performed sooner. Amniocentesis typically involves inserting a thin needle through the patient's abdominal wall through the wall of the uterus into the amniotic sac under ultrasound guidance during the 16-20 week of pregnancy. The CVS procedure may be carried out 10-13 weeks after the patient's last menstrual period. In the event that the fetus is found to be affected with a serious abnormality, earlier diagnosis allows for safer, and less emotionally traumatic, termination of the pregnancy due to the development of the fetus over time.

Chorionic villi are frond-like projections from the outer membrane or chorion of the anmiotic sac. These projections eventually form the placenta. Because chorionic villi are derived from the same fertilized egg as the fetus, they can be used to determine the genetic health of the fetus. The CVS procedure is done either by inserting a thin catheter, consisting of a cannula containing an obturator, under ultrasound guidance through the vagina and cervix into the chorionic villi of the chorion frondosum (transcervically), or by insertion of a thin needle through the abdominal wall (transabdominally). Once the cannula tip is placed within the chorion frondosum and the obturator is withdrawn, negative pressure is applied by some means, such as a syringe, to aspirate a sample of chorionic villi. Both methods of the CVS procedure may be done in a matter of minutes.

Biopsy catheters for use in the CVS procedure have heretofore been disclosed or manufactured in a number of ways. U.S. Pat. No. 5,106,377 to Martin describes various types. One such existing catheter consists of a hollow flexible cannula and a 1.5 millimeter diameter flexible aluminum obturator, which fits snugly in the cannula to facilitate inserting the cannula into position. When in use, the physician inserts the obturator into the cannula and then bends the resulting catheter to obtain the desired degree of bend for insertion into the patient. After the resulting catheter is maneuvered into the correct position, the obturator is withdrawn. The Martin patent mentions that a drawback of this catheter is the aluminum obturator tends to flex the curved portion of the cannula when removed, thus deflecting the cannula tip from the desired location.

Another catheter disclosed in the Martin patent consists of a malleable silver cannula that contains a flexible blunt stainless-steel obturator during insertion. The obturator supports the cannula to permit the cannula to be flexed without kinking thereby ensuring the tubular cannula's internal continuity. Likewise, with this catheter the stiffness of the obturator causes deflection of the cannula tip during withdrawal of the obturator. Additionally, the stiffness of the catheter would often cause ruptures in patients' membranes.

Yet another catheter disclosed in the Martin patent uses an aluminum obturator in a flexible plastic cannula that may be bent to the desired degree of curvature. Once again, when the obturator is removed its relative stiffness will cause flexing in the cannula and movement of the tip. Therefore, it has been previously disclosed that biopsy catheters for use in the CVS procedure, which use an obturator having greater stiffness than the cannula, may suffer from the disadvantage of tip displacement when the obturator is withdrawn.

U.S. Pat. No. 4,756,708, also to Martin, purportedly overcame this disadvantage with a preformed curved cannula and a very flexible obturator, which did not cause deflection of the cannula tip upon removal. However, this catheter was found not to work in all cases because the preset curvature angle did not fit the anatomy of some patients. Martin sought to remedy this with the catheter disclosed in U.S. Pat. No. 5,106,377. The catheter disclosed therein consists of an obturator of a synthetic plastic material such as polyurethane. The cannula consists of an outer sleeve of Nylon with an inner tube of a thin wall stainless steel. After inserting the obturator into the cannula the catheter is bent to the desired angle of curvature before maneuvering the catheter into position to collect the chorionic villi sample. The stiffer cannula construction was to prevent deflection of the tip when the obturator is removed. The stiffness of this catheter, however, was found by some practitioners to be undesirable.

Another form of CVS catheter is produced by Cook Urological in Spencer, Ind. This product, which is designated the Cook Chorionic Villus Sampling Set, consists of a hollow cannula with a malleable metal obturator. The catheter is manufactured in 1.9 millimeter and 1.8 millimeter diameters. The 1.9 millimeter size is available in 21 centimeter and 27 centimeter lengths. The 1.8 millimeter catheter is 24 centimeters in length. The obturator for each of these catheters includes a flat molded plastic handle. Because the handle is flat, it is difficult to manipulate between the fingers of the physician/operator when inserting the catheter to the desired location to collect the sample. The difficulty in manipulating this flat handle has been found to make placement of the catheter less precise in certain anatomical positions of the pregnant uterus.

INVENTION SUMMARY

Briefly, and in general terms, this invention relates to an improved catheter for sampling an area of interest, for example, for use in Chorionic Villus Sampling (CVS) or other uterine biopsy medical procedures. The catheter may be comprised of a cannula of flexible plastic that is non-pyrogenic and latex-free, and a flexible stainless steel obturator with a molded handle adapted for ease of manipulation by the operator and a steering guide to assist the operator in locating the cannula tip in the chorion frondosum. The cannula can easily be used with a visualization device or method to aid in guidance of the obturator, as an example, it can be echogenic and readily used with ultrasound. The catheter can be inserted through the cervix into the uterus during pregnancy, for example, at 10-13 weeks gestation, and guided into the developing placenta under some guidance means, for example, ultrasound. Once the catheter has been guided into place, the obturator is withdrawn and a sample of the area of interest, for instance, the chorionic villi, is removed by applying extraction method using applicable pressure, such as negative pressure, to the proximal end of the catheter and slowly withdrawing the catheter from the uterine cavity.

DETAILED DESCRIPTION OF EXEMPLARY EMBODIMENTS

The present invention is directed to a catheter for use in sampling an area of interest, such as the chorionic villus sampling procedure or other uterine biopsy medical procedures, comprising a cannula readily adjustable by the operator to conform to the patient's anatomy and that remains in place when the obturator is removed to collect the sample, and an obturator with a generally cylindrical handle and steering guide to allow the operator ease of manipulation and placement of the catheter at the area of interest, for example, the chorion frondosum.

By way of explanation and example, the present invention will be described in detail below. It is to be understood, however, that the present invention is not limited to the specific structure described herein as will be evident to one of ordinary skill in the relevant art.

Figure 1:
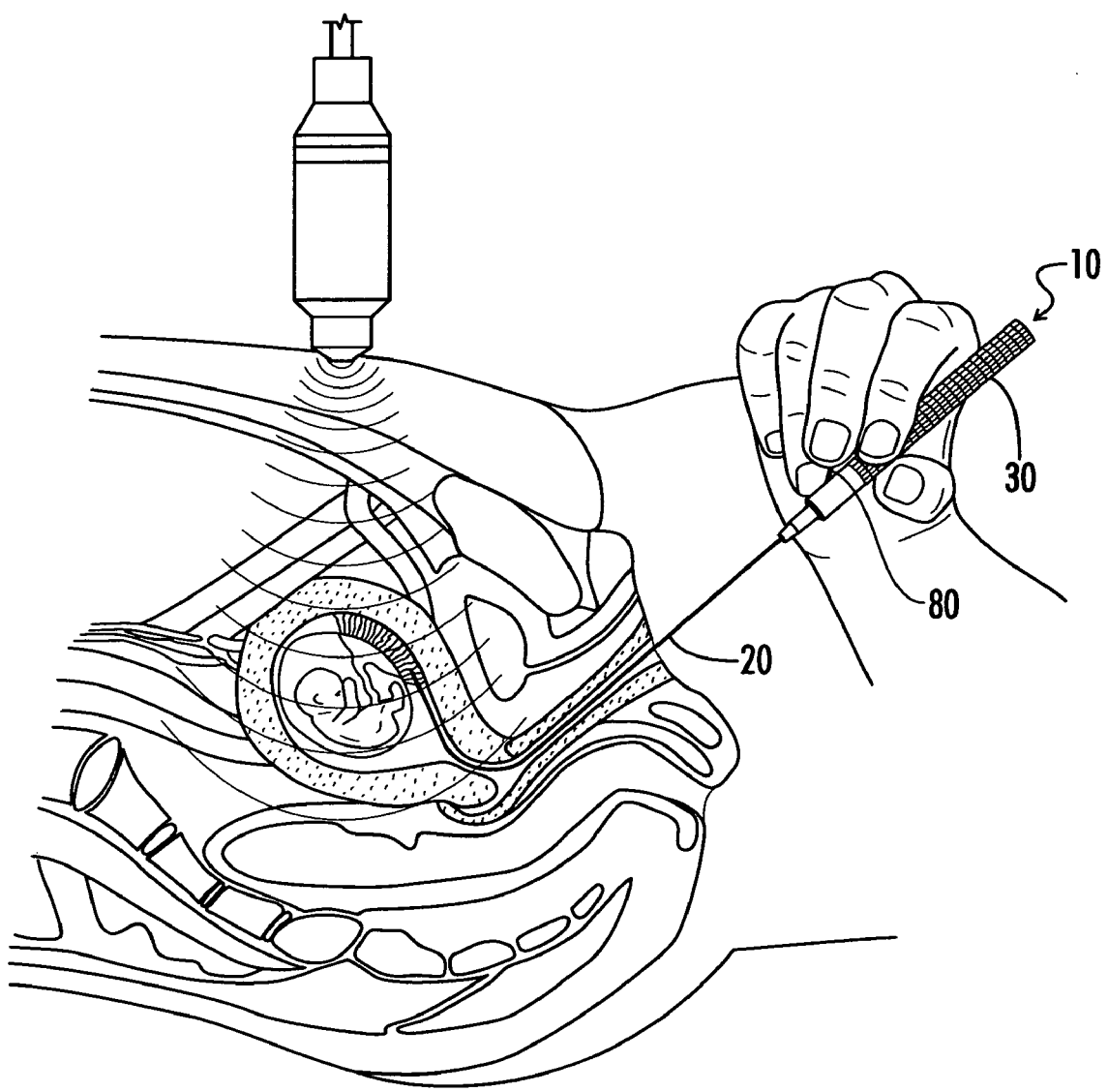
FIG. 1 is a diagrammatic view of the chorionic villus sampling procedure showing the physician inserting a preferred embodiment of the catheter of the present invention under ultrasound guidance into position to collect a sample of the chorionic villi.

FIG. 1 is a diagrammatic view of an embodiment of the catheter of the present invention being inserted with the aid of a visualization or imaging device, for example ultrasound, for guidance into position to collect a sample. The distal end of the cannula 100 is shown proximate the chorion villi. The cannula 20 is also shown to have been bent appropriately to conform to the anatomy of the patient. The bend in the cannula 20 is placed to correspond with the location of the handle guide 80 so that the operator may better locate the distal end of the cannula 100 after it has been inserted into the patient. After the distal end of the cannula 100 is properly placed, the obturator 40, which is fixedly attached to the handle 30, is withdrawn by disengaging the connector 130 by pulling the handle 30 while holding the proximal end of the cannula 120 in place. A syringe or some other device capable of imparting applicable pressure, such as negative pressure, is then attached to the proximal end of the cannula 120 and applied to draw villi into the distal end of the cannula 100. The cannula 20 is then slowly withdrawn from the uterine cavity.

Figure 2:
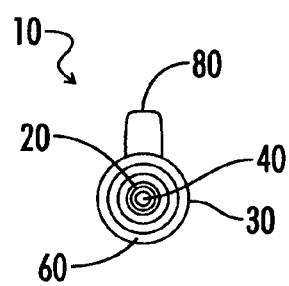
FIG. 2 is a front elevation view of a preferred embodiment of a catheter of the present invention.

FIG. 2 is a front elevation view of a preferred embodiment of the catheter 10 of the present invention showing the guide 80, consisting of a flange in this embodiment, at the twelve o'clock position atop the handle 30 and the catheter pointing toward the viewer. Also shown is a frontal view of cannula 20, obturator 40, and distal end of handle 60.

Figure 3:
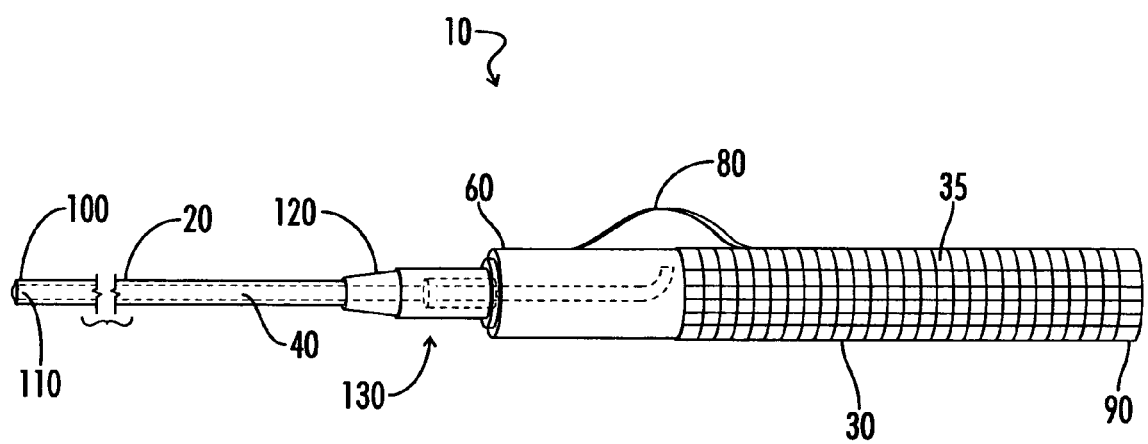
FIG. 3 is a side elevation view of a preferred embodiment of the catheter of the present invention.

FIG. 3 is a side elevation view of an embodiment of the catheter 10 of the present invention showing the relationship between the obturator handle 30 and the cannula 20. As shown, the obturator guide wire 40 (dotted lines) fits through the lumen of the cannula 20 and the connector 130, comprising in this embodiment a female luer hub at the proximal end of the cannula 120 and a male luer tip at the distal end of the handle 60 and fixedly attached to the handle 30. Those skilled in the art will appreciate that other means of incorporating a connector between the cannula 20 and obturator handle 30 may be used. The obturator handle 30 is configured to be generally cylindrical and contain on at least a portion thereof a textured grip 35 to enhance feel sensitivity, improve manipulation and promote improved precision and control in placing the catheter 10 during the procedure. In this embodiment of the catheter 10 of the present invention, the proximal 1¾ inches of the obturator handle 30 contains said texturing. The texturing may be accomplished by numerous mean as will be apparent to one skilled in the art. These methods may include providing raised areas along the surface of the handle 30 or covering a sections of the grip with a rubberized material or polymer.

By way of example, an embodiment of the catheter 10 of the present invention consists of a cannula 20 typically made of soft plastic such as a flexible polyurethane urea polymer and measures approximately 1.7 millimeters in diameter and 27 centimeters (10.5 inches) in length from its distal end 100 to the distal end of the handle 60. The cannula 20 may be constructed from plastic that is non-pyrogenic and latex-free. The cannula 20 and the handle 30 are releaseably attached by a connector 130. In the embodiment shown in FIG. 3 the connector 130 consists of a molded plastic female luer hub molded onto the proximal end of the cannula 120 and a molded plastic male luer tip molded onto the distal end 60 of the handle. The obturator 40 may be made of surgical grade stainless steel measuring 1.0 millimeters in diameter and 27.1 centimeters in length with a rounded, polished smooth tip at its distal end. The handle 30 may be made of hardened plastic and measures approximately 9.0 millimeters (0.3 inches) in diameter and 6.0 centimeters (2.3 inches) in length. The handle 30 also contains a guide 80 on the surface thereof proximate the distal end 60. This guide 80 facilitates aligning the curvature applied by the operator to the distal end of the cannula 100 and obturator 110 with the handle 30 for reference in steering the catheter 10 during placement. In an embodiment the guide 80 may be a flange measuring 15 millimeters by 4 millimeters by 2 millimeters. In another embodiment of the present invention the guide 80 may be formed containing other markings and features on the surface of the handle 30.

Referring to FIGS. 1, 2, and 3, in performing the CVS procedure with an embodiment of the catheter 10 of the present invention, the obturator wire 40 may be inserted into the lumen of the cannula 20 through the connector 130 so that its rounded distal end 110 terminates slightly past the distal end of the cannula 100 thereby plugging the distal end 100 and lumen. The operator is then able to bend the catheter 10 at an appropriate angle to fit the anatomy of the patient as shown in FIG. 1. The bend is made to correspond with the location of the guide 80 for reference in steering the catheter 10 during placement in the patient. Under visualization or imaging guidance, such as ultrasound, the operator maneuvers the distal end of the cannula 100 to the chorion frondosum to obtain the villi sample by holding the obturator handle grip 35 and rotating it as required. The operator then disengages the connector 130. In the embodiment shown, this is done by holding the connector 130 in place and pulling toward the proximal end of the obturator handle 90. As the male and female luer fitting is frictionally connected, this force causes the connector 130 to disengage. The obturator wire 40 may then be withdrawn by the operator through the lumen of the cannula 20. Next, applicable pressure, such as negative pressure, is applied to the proximal end of the cannula 120 by attaching an appropriate device such as a syringe to the female luer fitting. Accordingly, a villi sample is retrieved into the distal end of the cannula 100 and the operator slowly removes the catheter 10 from the patient.

In an embodiment of the present invention, the connector 130 contains luer friction fittings, which are standard on CVS catheters. In another embodiment of the present invention, the connector 130 may contain other types of connectors such as plastic screw in male/female fittings.

While the specification describes some embodiments of the present invention, those of ordinary skill may be able to devise variations of the present invention without departing from the scope of the invention. For example, the front view shape of the cylindrical handle as shown in FIG. 2 may be something other than circular, such as pentagonal, hexagonal, heptagonal, octagonal, and so on without departing from the scope of the invention. Accordingly, it is not intended that the invention be limited except as by the appended claims.

PARTS LIST

10 Catheter
20 cannula
30 handle
35 grip
40 obturator
60 distal end of handle
80 guide
90 proximal end of handle
100 distal end of cannula
110 distal end of obturator
120 proximal end of cannula
130 connector

What is claimed is:

1. A catheter for chorionic villus sampling, the catheter comprising:
   a flexible cannula of soft plastic having an elongate tubular body with a proximal end and an open distal end, a connector at said proximal end, and a lumen formed throughout the center of the tubular body and defined by the open distal end and extending through the connector at said proximal end, the tubular body being manually bendable to conform to a desired curvature; and
   an elongate obturator with a proximal end and a distal end, an elongate cylindrical handle at said proximal end of said obturator, said handle having a textured section at a proximal portion of the handle and a guide tab protruding from a distal portion of the handle and aligned with a bend in said cannula, said bend being introduced in said cannula by an operator of the catheter, and said guide tab functioning to keep track of said bend upon insertion of said cannula into a patient during chorionic villus sampling, and a malleable portion at the distal end of said obturator with a rounded smooth tip proportioned to close the open distal end of the lumen during insertion into the patient, the malleable portion thereof being slideably connectable to the cannula in the lumen and releaseably attached by the connector.

2. The catheter for chorionic villus sampling of claim 1, wherein said soft plastic of the cannula is non-pyrogenic and latex-free.

3. The catheter for chorionic villus sampling of claim 2, wherein said malleable portion of the obturator is flexible surgical grade stainless steel.

4. The catheter for chorionic villus sampling of claim 1, wherein said guide tab further comprising a flange.

5. A catheter for chorionic villus sampling, the catheter comprising:
   a cannula of a soft non-pyrogenic and latex-free plastic having a proximal end and an open distal end, a connector at said proximal end, and an elongate tubular body extending from the connector to the open distal end and defining with the connector a lumen extending throughout the center of the cannula, the tubular body being manually bendable to conform to a desired curvature; and
   an elongate obturator with a proximal end and a distal end, an elongate cylindrical handle at said proximal end of said obturator, the handle comprising a proximal end and a distal end with a textured grip at said proximal end of the handle, a guide tab on said distal end of the handle aligned with a bend in said cannula, said bend being introduced in said cannula by an operator of the catheter, and said guide tab functioning to keep track of said bend upon insertion of said cannula into a natural body orifice of a patient during chorionic villus sampling, and a malleable portion of stainless steel at the distal end of the obturator with a rounded smooth tip proportioned to close the open distal end of the lumen during insertion, the malleable portion thereof being slideably connectable to the cannula in the lumen and releaseably attached by the connector.

6. The catheter for chorionic villus sampling of claim 5, wherein said soft plastic of the cannula is a flexible polyurethane urea polymer.

7. The catheter for chorionic villus sampling of claim 6, wherein said malleable portion of the obturator is flexible surgical grade stainless steel.

8. The catheter for chorionic villus sampling of claim 5, wherein textured grip is plastic.

9. The catheter for chorionic villus sampling of claim 5, wherein said guide tab further comprising a flange.

10. The catheter for chorionic villus sampling of claim 9, wherein said cannula measures 1.7 mm in diameter and 27 cm in length, the connector further comprising a molded plastic female luer hub at the proximal end of the cannula and a molded plastic male luer tip at the distal end of the handle, the stainless steel portion of the obturator measuring 27.1 cm in length and 1.0 mm in diameter, the handle measuring 6.0 cm in length and 9.0 mm in diameter, and the flange measuring 15 mm by 4 mm by 2 mm.

11. An apparatus for uterine biopsy, comprising:
   a catheter for sampling an area of interest comprising a cannula with an elongate tubular body having a proximal end and an open distal end, a connector at said proximal end, and a lumen formed throughout the center of the tubular body defined by the open distal end and extending through the connector at said proximal end, the tubular body being manually bendable to conform to a desired curvature; and
   an elongate obturator in said catheter, with a proximal end and a distal end, an elongate cylindrical handle at said proximal end of said obturator, said handle having a textured section at a proximal portion of the handle and a guide protruding from a distal portion of the handle and aligned with a bend in said cannula, said bend being introduced in said cannula by an operator of the apparatus, and said guide functioning to keep track of the location of said bend and therefore also said open distal end of said cannula upon insertion into a natural body orifice of a patient during chorionic villus sampling, and a malleable portion at the distal end of the obturator, said malleable portion with a rounded smooth tip proportioned to close the open distal end of the lumen during insertion, the malleable portion thereof being slideably connectable to the cannula in the lumen and releaseably attached by the connector.

12. The apparatus of claim 11, wherein said cannula is flexible and made of soft plastic.

13. The apparatus of claim 12, wherein said soft plastic is a polyurethane urea polymer.

14. The apparatus of claim 12, wherein said soft plastic is non-pyrogenic and latex-free.

* * * * *